United States Patent [19]

Mebane

[11] Patent Number: 5,486,999
[45] Date of Patent: Jan. 23, 1996

[54] APPARATUS AND METHOD FOR CATEGORIZING HEALTH CARE UTILIZATION

[76] Inventor: Andrew H. Mebane, 75-683 Hua-ai, Kailua-Kona, Hi. 96740

[21] Appl. No.: 232,512

[22] Filed: Apr. 20, 1994

[51] Int. Cl.$^6$ .................................................. G06F 159/00
[52] U.S. Cl. .......................................... 364/401; 395/924
[58] Field of Search .............................. 364/401, 413.01, 364/413.02, 413.03; 395/21, 23, 924

[56] References Cited

U.S. PATENT DOCUMENTS

| | | |
|---|---|---|
| 4,464,122 | 8/1984 | Fuller et al. . |
| 4,733,354 | 3/1988 | Potter et al. . |
| 4,872,122 | 10/1989 | Altschuler et al. . |
| 4,945,476 | 7/1990 | Bodick et al. . |
| 4,965,725 | 10/1990 | Rutenberg . |
| 5,060,279 | 10/1991 | Crawford et al. . |
| 5,065,315 | 11/1991 | Garcia . |
| 5,175,796 | 12/1992 | Refregier et al. . |
| 5,175,797 | 12/1992 | Funabashi et al. . |
| 5,204,938 | 4/1993 | Skapura et al. . |
| 5,278,945 | 1/1994 | Basehore et al. . |
| 5,280,564 | 1/1994 | Shiomi et al. . |
| 5,280,566 | 1/1994 | Nakamura . |
| 5,282,261 | 1/1994 | Skeirik . |
| 5,283,855 | 2/1994 | Motomura et al. . |
| 5,285,524 | 2/1994 | Cok . |
| 5,287,272 | 2/1994 | Rutenberg et al. . |
| 5,287,430 | 2/1994 | Iwamoto et al. . |
| 5,289,563 | 2/1994 | Nomoto et al. . |
| 5,293,454 | 3/1994 | Kamiya . |
| 5,293,455 | 3/1994 | Castelaz . |
| 5,293,456 | 3/1994 | Guez et al. . |
| 5,293,457 | 3/1994 | Arima et al. . |
| 5,293,458 | 3/1994 | Chung et al. . |
| 5,293,459 | 3/1994 | Duranton et al. . |
| 5,295,229 | 3/1994 | Viot et al. . |
| 5,297,034 | 3/1994 | Weinstein . |
| 5,297,237 | 3/1994 | Masuoka et al. . |
| 5,299,121 | 3/1994 | Brill et al. . |
| 5,299,284 | 3/1994 | Roy . |
| 5,299,285 | 3/1994 | Tawel . |
| 5,299,286 | 3/1994 | Imondi et al. . |
| 5,299,287 | 3/1994 | Tsuruta et al. . |
| 5,303,328 | 4/1994 | Masui et al. . |
| 5,303,329 | 4/1994 | Mead et al. . |
| 5,303,330 | 4/1994 | Gersho et al. . |
| 5,305,424 | 4/1994 | Ma et al. . |
| 5,305,425 | 4/1994 | Ishida et al. . |
| 5,307,262 | 4/1994 | Ertel . |
| 5,311,876 | 5/1994 | Olsen et al. ............................ 128/731 |
| 5,313,558 | 5/1994 | Adams . |
| 5,313,559 | 5/1994 | Ogata et al. . |
| 5,315,505 | 5/1994 | Pratt et al. . |
| 5,317,506 | 5/1994 | Coutre et al. . |
| 5,317,675 | 5/1994 | Ikehara . |
| 5,317,676 | 5/1994 | Austvold et al. . |
| 5,319,739 | 6/1994 | Yoshiura et al. . |
| 5,325,293 | 6/1994 | Dorne . |
| 5,325,294 | 6/1994 | Keene . |
| 5,325,464 | 6/1994 | Pechanek et al. . |
| 5,327,341 | 7/1994 | Whalen et al. . |
| 5,327,522 | 7/1994 | Furuta et al. . |
| 5,329,611 | 7/1994 | Pechanek et al. . |
| 5,331,548 | 7/1994 | Rollema et al. . |

(List continued on next page.)

OTHER PUBLICATIONS

Katon, Wayne et al., "Distressed High Utilizers of Medical Care", *General Hospital Psychiatry*, 12, 355–362, 1990.

*Primary Examiner*—Donald E. McElheny, Jr.
*Attorney, Agent, or Firm*—Knobbe, Martens, Olson & Bear

[57] ABSTRACT

An apparatus and method for categorizing health care utilization provides an efficient aid in identifying patients who are seeking inappropriate care. The invention involves a computer system having a neural network responsive to several input variables to categorize the utilization characteristics of the patient. The input variables define selected characteristics of a patient. In one embodiment, a screening process identifies patients who are at high risk to an immediate threat to their health and eliminates those least likely to be seeking inappropriate care.

9 Claims, 6 Drawing Sheets

Microfiche Appendix Included
(6 Microfiche, 298 Pages)

U.S. PATENT DOCUMENTS

| | | |
|---|---|---|
| 5,331,550 | 7/1994 | Stafford et al. . |
| 5,335,172 | 8/1994 | Matsumoto et al. . |
| 5,335,173 | 8/1994 | Sasahara . |
| 5,337,369 | 8/1994 | Shibuya . |
| 5,337,395 | 8/1994 | Vassiliadis et al. . |
| 5,341,291 | 8/1994 | Roizen et al. . |
| 5,343,555 | 8/1994 | Yayla et al. . |
| 5,347,613 | 9/1994 | Chung et al. . |
| 5,349,646 | 9/1994 | Furuta et al. . |
| 5,353,382 | 10/1994 | Yariv et al. . |
| 5,353,383 | 10/1994 | Uchimura et al. . |
| 5,353,384 | 10/1994 | Yoshida . |
| 5,355,434 | 10/1994 | Yoneda et al. . |
| 5,355,435 | 10/1994 | DeYong et al. . |
| 5,355,436 | 10/1994 | Shin et al. . |
| 5,355,437 | 10/1994 | Takatori et al. . |
| 5,355,438 | 10/1994 | Takatori et al. . |
| 5,355,444 | 10/1994 | Chirico . |
| 5,355,528 | 10/1994 | Roska et al. . |
| 5,357,427 | 10/1994 | Langen et al. . |
| 5,357,597 | 10/1994 | Aparicio, IV et al. . |
| 5,359,699 | 10/1994 | Tong et al. . |
| 5,359,700 | 10/1994 | Seligson . |
| 5,361,202 | 11/1994 | Doue . |
| 5,361,326 | 11/1994 | Aparicio, IV et al. . |
| 5,361,328 | 11/1994 | Takatori et al. . |
| 5,363,473 | 11/1994 | Stolfo et al. . |
| 5,377,101 | 1/1994 | Rollema . |
| 5,379,366 | 1/1995 | Noyes . |
| 5,381,487 | 1/1995 | Shamos . |
| 5,381,515 | 1/1995 | Platt et al. . |
| 5,384,895 | 1/1995 | Rogers et al. . |
| 5,388,043 | 2/1995 | Hettinger . |
| 5,400,436 | 3/1995 | Nara et al. . |
| 5,404,292 | 4/1995 | Hendrickson . |
| 5,410,471 | 4/1995 | Alyfuku et al. . |
| 5,519,738 | 6/1995 | Shima et al. . |

FIG. 1

CATAGORIES OF CARE

| CATEGORY | I (PATIENT DRIVEN CARE) | II (A MIX OF PATIENT DRIVEN CARE AND ILLNESS DRIVEN CARE) | III (ILLNESS DRIVEN CARE) | IV (POSSIBLE PATIENT DRIVEN CARE) |
|---|---|---|---|---|
| QUESTIONAIRE SCORES | HIGH (ANX≥3 OR DEP≥3 OR SOM≥3) OR (TOTAL ADS≥6) | HIGH (ANX≥3 OR DEP≥3 OR SOM≥3) OR (TOTAL ADS≥6) | LOW (ANX<3 AND DEP<3 AND SOM<3) AND (TOTAL ADS<6) | LOW (ANX<3 AND DEP<3 AND SOM<3) AND (TOTAL ADS<6) |
| ILLNESS DRIVEN DIAGNOSIS | NONE | PRESENT | PRESENT | NONE |
| DIFFERENT DIAGNOSTIC RANGES ≥6 FOR <60 YEARS OLD ≥8 FOR ≥60 YEARS OLD | POSSIBLE | POSSIBLE | POSSIBLE | PRESENT |
| DEFINITE PATIENT DRIVEN DIAGNOSIS | POSSIBLE | POSSIBLE | NONE | POSSIBLE |
| POSSIBLE PATIENT DRIVEN DIAGNOSIS (2 OR MORE) | POSSIBLE | POSSIBLE | LESS THAN 2 | POSSIBLE |

APPARATUS AND METHOD FOR CATEGORIZING HEALTH CARE UTILIZATION

Microfiche Appendix: Appendix B is a microfiche appendix of six microfiche and 298 frames.

BACKGROUND OF THE INVENTION

1. Field of the Invention

The present invention relates generally to a system of categorizing health care utilization, and more particularly, to an apparatus and method of identifying health care utilization using a neural network processor.

2. Description of the Related Art

Inappropriate utilization of health care services in the United States wastes scarce financial and medical resources. One common cause of such inappropriate utilization occurs when patients seek treatment of one physical condition, when, in fact, their symptoms result from an obscured underlying etiology such as alcoholism or psychiatric illness. For instance, an alcoholic may continually seek treatment for physical ailments resulting from alcohol abuse, while the actual problem of alcoholism remains undiagnosed. Inappropriate utilization of medical resources under such circumstances is referred to herein as PATIENT DRIVEN CARE ("PDC").

In contrast, the appropriate utilization of health care and medical resources through treatment of ailments without obscured underlying causes is referred to herein as ILLNESS DRIVEN CARE ("IDC").

Systems have been proposed which utilize computers for classification of patients or which utilize expert systems for diagnosis purposes. For instance, U.S. Pat. No. 4,464,122 to Fuller, et al. discloses the concept of using a computerized system for analyzing health care questionnaires. In addition U.S. Pat. No. 4,730,259 to Gallant discloses the use of a general purpose matrix-controlled expert system which uses a base of knowledge to make inferences from input information until an appropriate response can be deduced. However, these systems do not identify inappropriate utilization.

SUMMARY OF THE INVENTION

The present invention recognizes the potential savings from identification of inappropriate utilization from patient driven care. Preferably, through application of the teachings of the present invention, patients utilizing health care appropriately and patients utilizing health care inappropriately can be separated. Identification of patient driven care utilizers alerts the attending physician of the probability that a patient has an undiagnosed underlying ailment. This knowledge facilitates diagnosis and efficient treatment of the patient's underlying disorders, rather than the associated apparent physical disorders associated with the underlying disorder. As a result, scarce financial and medical resources may be efficiently utilized, and a patient's ailments may be promptly treated.

One aspect of the present invention involves a system to aid in identifying patients potentially seeking inappropriate health care. The system operates on a plurality of patient characteristics for a plurality of patients. The patient characteristics represent medical usage and psychological information about the patients. A neural network responds to input variables generated from the plurality of patient characteristics. The neural network is configured and adapted to recognize patterns among the variables to aid in categorizing the plurality of patients according to utilization characteristics of the patients based on the input variables. One of utilization categories identifies patients who are potentially seeking inappropriate health care.

In the present embodiment, the patients are categorized into groups consisting of: patients seeking patient driven care, patients seeking illness driven care, patients seeking a mix of patient driven care and illness driven care, and patients seeking possible patient driven care.

Another aspect of the present invention involves a method to aid in the categorization of health care utilization of a plurality of patients. The method involves a number of steps. A set of input variables having input values which define selected characteristics of each patient are defined. The input variables have some correlation to the health care utilization of each of the plurality of patients. The input variables are analyzed to identify those patients who are seeking inappropriate health care utilization. A list of the identified patients is provided to a case manager for further health care management. In one embodiment, the input variables form an input vector to a neural network trained to help identify the plurality of patients according to health care utilization based upon the input variables. In a further embodiment, the plurality of patients are first pre-screened based upon a set of pre-screening variables to eliminate those patients among the plurality of patients who are most likely at immediate risk to their health.

Preferably, at least one of the pre-screening variables comprises a variable indicative of the existence of at least one alcohol or drug addiction disorder. More preferably, another of the pre-screening variables comprises a variable representing anxiety, depression and/or somatization.

Yet another aspect of the present invention involves a method of training a neural network to aid in categorizing health care utilization of a plurality of patients. The training method involves a sequence of steps. More particularly, a set of input variables having input values which define selected characteristics of each of the plurality of patients is defined. The plurality of patients form a training set for the neural network. At least two categories of health care utilization are defined for the plurality of patients. Which of the at least two categories applies to each of the plurality of patients is then determined, preferably by a health care professional; and the applicable category for each patient becomes a target value for the neural network analysis for each patient. The input variables for each patient and target value for each patient are then provided to the neural network. The input variables are then analyzed with the neural network for each of the patients to obtain first corresponding output values associated with each patient. The first corresponding output values are compared to the target output values. Then, the weights in the neural network are adjusted if the first corresponding output values do not approximate the target output value. Preferably, the weight adjustments partially compensate for the difference between the target output values and the first corresponding output values.

These steps are repeated until the first corresponding output values are substantially the same as the target output values or no more improvement is attained.

In one embodiment, the selected characteristics are selected from the group consisting of: anxiety, depression, somatization, frequency of use, type of use, and cost of use of health care services.

In the present embodiment, the at least two categories are selected from a group consisting of: patient driven care, illness driven care, a mix of patient driven care and illness driven care, and possible patient driven care.

Additional aspects of the present invention will be apparent in connection with the description of the preferred embodiments.

DETAILED DESCRIPTION OF THE PREFERRED EMBODIMENT

In general, the present invention involves performing an analysis based on several factors relating to a patient's lifestyle and health care utilization to identify inappropriate health care utilization. In one embodiment, the analysis is performed using a neural network processor trained to map the several factors to different categories of health care utilization. In particular, the present invention provides a method and apparatus to help distinguish appropriate use from inappropriate use of the health care system, based on selected characteristics and medical usage of patient driven care and illness driven care utilizers. The selected characteristics and patterns provide guidelines which indicate the presence of underlying disorders such as depression, alcoholism, and somatization.

Preferably, several factors representing the selected characteristics and medical usage patterns become input variables, often called an input vector, for the neural network processor. A category of care for the individual represented by each input vector becomes the corresponding target output for the neural network. The collection of input and corresponding output pairs comprise the training set for the neural network. Based upon a large training set, the neural network "learns" to identify patterns which help distinguish categories of health care utilization of the patients in the training set.

In one embodiment, the neural network classifies patients' utilization of health care into at least two categories: patient driven care and illness driven care. In a preferred embodiment, four categories are identified: (1) patient driven care, (2) a mix of patient driven and illness driven care, (3) illness driven care, and (4) possible patient driven care. Although additional categories may also be established, for present purposes, these four categories are disclosed.

Figure 1:
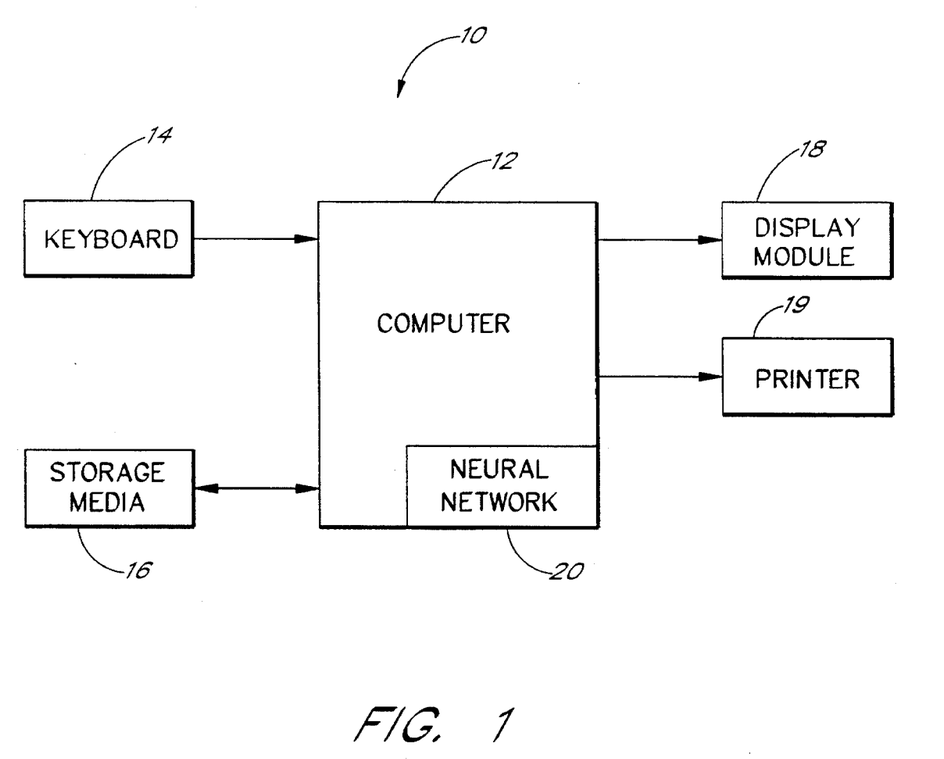
FIG. 1 depicts a block diagram of one embodiment of a processing system used in accordance with the present invention.

FIG. 1 illustrates a processing system 10 for use in the present invention. The processing system 10 comprises a computer 12, which is adapted to receive input data from an operator by means of a keyboard 14 or from other sources such as a patient database (not shown) stored on mass storage media 16. The storage media 16 may also be used to store output data from the computer 12. In addition, the computer 12 is coupled to a display module 18. The display module may be a computer monitor or similar device. The categorization system 10 further comprises a printer 19.

The computer 12 is conventional and executes a simulation of a neural network 20. Typical computers include a general purpose desk-top computer such as a Hewlett-Packard computer, a SUN computer or an IBM computer. The computer 12 may also be a mainframe computer, a server or a workstation. In one embodiment, the computer 12 is connected to a Local Area Network ("LAN") or a Wide Area Network ("WAN"). Thus, the information generated by the processing system 10 may be accessible from any computer on the LAN or WAN and may be accessed or assimilated by existing database management software. The processing system 10 may also include various other input/output ("I/O") and peripheral modules which are coupled to the computer 12, as known in the art.

The neural network 20 used in the present invention is a software simulation of a collection of processing elements, as is well understood in the art. Inputs are provided to each processing element, which in turn generates a single output. This single output may then be provided along numerous pathways as an input to other processing elements, connecting the processing elements into a network. Each input is assigned a relative weight, as well understood in the art. Any one of several different neural network models which use supervised training can be used.

The neural network 20 is trained to process information through exposure of the network to input data and corresponding target output data (referred to above as the "training set"). During the training phase, the network is supplied with input data with corresponding answers (the expected or target output) as examples. For each input vector in the training set of input vectors, the network compares its output from processing the vector with the expected output and adjusts its weights to minimize the error in the response.

In one embodiment, back-propagation training is used. With back-propagation, the error signal is generated and back propagated through the levels of the network. During back-propagation, the weights given to each input at each level are adjusted in an attempt to compensate for the error. Another input vector and corresponding expected output value from the training set is passed to the network, and the resultant error signal is back propagated through the network. Alternatively, the weight adjustments may be accumulated and applied after all the training examples have been presented to the neural network, as is understood in the art.

This process is iterated until the output error reaches an acceptable level, or no further improvement is noted. The size of the training set is generally chosen to provide an acceptable level of confidence in the neural network output for the given application.

In general, in the present embodiment, the training set comprises a large number of input vectors, each input vector representing the selected characteristics and medical usage of a selected patient, and a corresponding expected output (target output vector) for the neural network 20. The neural network "learns" by adjusting its weights in a manner which is targeted to produce the correct response for each of the samples in the training set. The objective is to have the network produce the correct response (correct classification) for new objects which it has not analyzed during training. After training, the neural network may be used to process new information.

The neural network 20 utilized in the present invention may be implemented in different ways known in the art. The neural network may be implemented in software. Neural network programs are available from several suppliers. One such supplier is NeuralWare, Inc. located in Sewickley, Pennsylvania. A neural network may also be written in conformance to well understood neural network models, such as those described in James A. Freeman and David M. Skapura "Neural Networks, Algorithms, Applications and Programming Techniques," 1992. In one embodiment, the neural network of the present invention comprises a multi-layer artificial neural network of the back-propagation type, as well understood in the art. The neural network 20 may also comprise a dedicated processor, as understood in the art. Advantageously, the neural network 20 of the present invention comprises non-linear activation functions in at least the hidden layers. Linear or non-linear activation functions for the output layers of the neural network can be used depending upon the desired type of response.

In order to train the neural network 20 of the present invention, appropriate input variables are selected. In general these input variables are discussed with reference to a Lifestyle Questionnaire and data from a patient's medical utilization records. An exemplary Lifestyle Questionnaire, designed to determine the selected lifestyle characteristics (i.e., the psychological make-up) of the patient, is provided in Appendix A. Details of the Questionnaire are discussed below.

In the present embodiment, the selected input variables are provided to the categorization system 10 depicted in FIG. 1 in one of two ways: by operator input via the keyboard 14 or from an existing patient database stored on the storage media 16. In one embodiment, the patient database comprises a plurality of patient files, each of which contains the input vector for the represented patient. This information is processed by the neural network 20 (or other means) to categorize health care utilization, as will be described in detail below. The categorization results are presented on display module 18. Alternatively, the results may be stored in a patient database on the storage media 16, or printed on the printer 19 in an organized format.

In a preferred embodiment, the categorization system 10 may be utilized to prescreen patients prior to processing of the patient data by the neural network 20. In this embodiment, patients deemed at high risk (of having patient driven care tendencies) or patients who engage in extremely frequent utilization of medical services are identified and forwarded to a case manager for review.

Some of the input variables taken from the patient medical records relate to the type of diagnoses a patient has been given. Appendix B (microfiche) depicts a list which provides a proposed classification of well known patient diagnoses into the following four categories: (1) illness driven diagnoses, (2) definite patient driven diagnoses, (3) possible patient driven diagnoses and (4) diagnoses of no interest. In each category, a number of diagnoses associated with each class of diagnoses are listed and coded numerically. These codes are utilized in a patient's medical records to facilitate the classification of that patient's utilization of health care, as described in detail below.

As mentioned above, in the present invention, the neural network developed during the training phase utilizes a number of input variables taken from information in the patient's medical database as well as information from the Lifestyle Questionnaire. The input variables used to form input vectors for the present embodiment are listed in Table 1.

TABLE 1

INPUT VECTOR VARIABLES

| Variable Number | Variable Name | Range | Format[1] |
| --- | --- | --- | --- |
| 1 | Anxiety | 0–5 | d |
| 2 | Depression | 0–5 | d |
| 3 | Somatization | 0–5 | d |
| 4 | Total ADS | 0–15 | dd |
| 5 | Age | 18–100+ | ddd |
| 6 | Sex | M = 0, F = 1 | b |
| 7 | Gross Charges Total | 0–99999[2] | ddddd |
| 8 | Total Count | 0–9999 | dddd |
| 9 | Gross Charges Out-Patient | 0–99999[2] | ddddd |
| 10 | Out-Patient Count | 0–9999 | dddd |
| 11 | Gross Charges DOV | 0–99999[2] | ddddd |
| 12 | DOV Count | 0–9999 | dddd |
| 13 | Gross Charges Non-DOV | 0–99999[2] | ddddd |
| 14 | Non-DOV Count | 0–9999 | dddd |
| 15 | Number of different PCP's seen | 0–99 | dd |
| 16 | Number of different specialists seen | 0–99 | dd |
| 17 | Number of different Out-Patient Diagnoses | 0–999 | ddd |
| 18 | Number of in-patient or out-patient diagnostic ranges | 0–19 | dd |
| 19 | Patient Driven Definite | yes = 1; no = 0 | b |
| 20 | Illness Driven | yes = 1; no = 0 | b |
| 21 | Patient Driven Possible | yes = 1; no = 0 | b |

[1]"d" denotes one decimal digit (0–9); "b" denotes one binary digit (0–1)
[2]hundreds of dollars, rounded to the nearest $100.00

Table 1 also provides information on the organization of each patient input vector data file. As shown in Table 1, each input variable is assigned by a variable number. Each input variable also has a range and a data format. The format column describes the representative format for the variable in the input vector data files. For example, the input variable 1, "Anxiety," may have a value ranging from –5 (see "Range" column), whereby "0" indicates no anxiety and "5" indicates extreme anxiety. This value is represented in an input vector data file by a single decimal digit ranging from 0–5. This is illustrated in Table 1 by the single "d" reference in the "Format" column.

In the present embodiment, twenty-one variables have been selected for the input vectors for the neural network 20 for categorization purposes. In the present embodiment, each of the input vector variables is scaled to a value ranging from "−1" to "1." Alternatively, the input vector variables are scaled to values ranging from "0" to "1" or "−1" to "0." For instance, in the embodiment where the scaling is for the range of −1 to 1, and the range of raw values for a variable is 1–5, the raw value "1" will scale to −1 and the raw value "5" will scale to 1. This type of scaling for neural networks is well understood in the art.

These twenty-one input vector variables, each of which represents a particular characteristic of a patient, are: Anxiety ("ANX"), Depression ("DEP"), Somatization ("SOM"), Combined Values of Anxiety, Depression and Somatization ("TOTAL ADS"), Age, Sex, Total Gross Charges, Total number of line item charges ("Total Count"), the Total Out-Patient Gross Charges, the total number of Out-Patient Visits ("Out-Patient Count"), the Total Gross Charges attributable to Doctor Office Visits ("Gross Charges DOV"), the number of Doctor Office Visits ("DOV Count"), the Total Gross charges attributable to Non-Doctor Office Visits ("Gross Charges Non-DOV"), the number of non-Doctor Office Visits ("Non-DOV Count"), the number of different Primary Care Physicians ("PCP") seen, the number of different specialists seen, the number of different Out-Patient Diagnoses, the number of inpatient or out-patient diagnostic ranges, whether definite patient driven care diagnoses are present ("Patient Driven Definite"), whether illness driven care diagnoses are present ("Illness Driven"), and whether possible patient driven care diagnoses are present ("Patient Driven Possible").

The values of the first four input vector variables (Anxiety, Depression, Somatization, and total ADS) are obtained from various answers provided by the patient to the Lifestyle Questionnaire. In the Questionnaire, five questions relating to the patient's anxiety, depression and somatization are listed. These questions are designed to provide some information about the psychological make-up of the patient.

With reference to the Lifestyle Questionnaire in Appendix A, five questions (questions 21–25) in the Lifestyle Questionnaire are designed to determine the anxiety level of a patient. Each affirmative response to questions 21 through 25 indicates that the patient experiences a certain level of anxiety. A score of "1" is assigned to each affirmative response and a score of "0" is assigned to each negative response. A sum of the values for questions 21–25 becomes the value for the input variable number 1, the Anxiety variable. Thus, as explained above, the value of the input variable for Anxiety may range from 0–5, whereby a score of 0 indicates that the patient experiences no or very little anxiety and a score of 5 indicates that a patient experiences substantial anxiety.

As shown in the Lifestyle Questionnaire in Appendix A, questions regarding depression and somatization are listed to identify the existence of these psychological ailments in a patient. Questions 26–30 of the Lifestyle Questionnaire in Appendix A relate to the Depression input variable depicted in Table 1. Questions 31–35 relate to the Somatization input variable from Table 1. As with the Anxiety variable, because there are five questions which relate to depression and to somatization, the Depression input variable and the Somatization input variable each has a range from 0–5, as depicted in Table 1.

The score of the Anxiety, Depression, and Somatization input variables are summed to generate the Total ADS variable listed in Table 1. Thus, the Total ADS variable has a range of 0–15.

The values of the variable numbers 5 and 6, Age and Sex, are also obtained from information listed in the Lifestyle Questionnaire or can be obtained from patient medical records. The Age input variable, variable number 5, ranges from 18 to 100+. This value is represented in the data file by three decimal digits. The Sex input vector variable, variable number 6, is defined as having a value of 0 for male and 1 for female. This variable is represented with a single binary digit (0 or 1) in the patient input vector data file (represented by the single "b" in the Format column).

The values of variable numbers 7–18 are advantageously obtained from the patient's medical records. The "Gross Charges" variable, variable number 7, refers to the gross dollar amount of charges that the patient has incurred through his or her use of health care. The value for this variable is recorded in hundreds of dollars and ranges from 0–99999. As illustrated in Table 1, this value is represented with five decimal digits in the data file for each patient.

The "Total Count" variable, variable number 8, refers to the total number of line item charges that the patient has incurred. This value has a defined range from 0–9999 and is represented with four decimal digits in each data file.

The "Gross Charges Out-Patient" variable, variable number 9, represent the Total Out-Patient Gross Charges incurred. The value of this variable is recorded in each patient data file in hundreds of dollars ranging from 0–99999 in a field in the data file having five decimal digits.

The "Out-Patient Count" variable, variable number 10, represents the total number of out-patient visits of the patient. In the present embodiment, out-patient visits refers to the combined number of doctor office visits and non-doctor office visits (any medical encounter without visiting the attending physician, such as lab work). The value of this variable is listed in the data file with a from 0–9999 in a field of having four deemed digits.

The "Gross Charges DOV" variable, variable number 11, represents the total dollar charges attributable to doctor office visits by the patient. The value of this variable is listed in the patient data file in hundreds of dollars, ranging from 0–99999 in a field in the data file of five decimal digits.

The "DOV Count" variable, variable number 12, refers to the number of times a patient has visited a doctor at his or her office. The value of this variable is listed as a number in the patient data file ranging from 0–9999, in a field having four decimal digits.

The "Gross Charges Non-DOV" variable, variable number 13, represents the total charges attributable to non-doctor office visits. In the present embodiment, a non-doctor office visit is any medical encounter which did not involve the attendance of a physician, including visits to laboratories for medical testing. The value of this variable is listed in the data file in hundreds of dollars, ranging from 0–99999, in a field having five decimal digits.

The "Non-DOV Count" variable, variable number 14, represents the number of non-doctor office visits by a patient. The value of this variable is listed in the patient data file, ranging from 0–9999, in a field having four decimal digits.

The "number of PCP's seen" variable, variable number 15, represents the number of different primary care physicians seen by a particular patient. The value of this variable is listed in the data file, ranging from 0–99, in a field having two decimal digits.

The "number of different specialists seen" variable, variable number 16, represents the number of different specialists seen by a patient. The value of this variable is listed in the data file, ranging from 0–99, in a field having two digits.

The "number of different Out-Patient Diagnoses" variable, variable number 17, refers to the number of outpatient diagnoses made by physicians seen by the patient. The value of this variable is listed in the data file, ranging from 0–999, in a filed having three digits.

The "number in-patient or out-patient diagnostic ranges" variable, variable number 18, represents the number of predetermined ranges into which in-patient or out-patient diagnoses for a patient are classified. As well understood in the art, there are several predefined diagnostic ranges for different organ systems in the human body (e.g., Infectious and Parasitic Disease, Neoplasms Endocrine, nutritional and metabolic diseases, etc.). The diagnostic ranges of the present embodiment are listed in Appendix C. The diagnoses that fall into each range are recorded in each patient's medical records. The patient receives a count of "1" for each different range in which the patient has diagnoses. The total number of ranges into which diagnoses for a patient are categorized is the value for variable number 18. The value of this variable is listed in the data file, ranging from 0–19, in a field having two decimal digits.

The "Patient Driven Definite" variable, variable number 19, represents whether any definite patient driven diagnoses are present. An exemplary list of definite patient driven diagnoses is provided in Appendix B. The value of this variable is represented in a patient data file with a binary digit, where yes=1 and no=0.

The "Illness Driven" variable, variable number 20, represents whether any illness driven diagnoses are present. An exemplary list of illness driven diagnoses is provided in Appendix B. The value of this variable is represented in a patient data file with a binary digit, where yes=1 and no=0.

The "Patient Driven Possible" variable, variable number 21, represents whether any possible patient driven diagnoses are present. An exemplary list of possible patient driven diagnoses is provided in Appendix B. The value of this variable is represented in a patient data file with a binary digit, where yes=1 and no=0.

TABLE 2

| Variable Number | Variable Name | Range | Format[1] |
|---|---|---|---|
| 1 | category 1 | Yes = 1, No=0 | b |
| 2 | category 2 | Yes = 1, No=0 | b |
| 3 | category 3 | Yes = 1, No=0 | b |
| 4 | category 4 | Yes = 1, No=0 | b |

As briefly explained above, in order to train a neural network a correct output or output vector is provided for each input vector in a training set. TABLE 2 is a format chart of patient output vectors for the neural network 20. The output vector basically describes the category of care for the patient. In the present embodiment, the output vector comprises the values corresponding to the four categories of health care utilization described above. Category 1 represents Patient Driven Care, Category 2 represents a combination of Patient Driven Care and Illness Driven Care, Category 3 represents Illness Driven Care and Category 4 represents Possible Patient Driven Care. It will be understood that additional categories are also envisioned, and the particular categories selected do not limit the scope of the present invention.

As illustrated in TABLE 2, each category of care is assigned a value of 0 or 1, where 0 indicates that a particular category of care is inapplicable and 1 indicates that the patient is classified in that category of care. Preferably, for any given input vector, only one category in the output vector has a value of 1. In other words, only one category of the four categories listed applies for any given patient.

TABLE 3

```
Column Number
00000000011111111112222222222333333333344444444445555555555666666666677777777778888888
12345678901234567890123456789012345678901234567890123456789012345678901234567890123456
 5 2 4 22 41  1 1129 473 378 468 21 26 355 422 4 3 23 10 0 1 1 0 1 0 0
Input Var Number                                                               Out. Var Number
 1 2 3 44 555 6 77777 8888 99999 1111 11111 1111 11111 1111 11 11 111 11 1 2 2 1 2 3 4
                                    0000 11111 2222 33333 4444 55 66 777 88 9 0 1
```

As mentioned above, information for each patient is represented in a patient data file which is configured to be read by the computer 12. For training purposes, the data file for each patient in the training set includes the expected output vector. For patients to be analyzed after training, the output vectors are unknown, and provided by the neural network 20. An exemplary patient data file format is illustrated in TABLE 3. In TABLE 3, the Column Number, Input Var Number and Output Var Number labels, and corresponding reference indexes are provided for ease of description. The column numbers in TABLE 3 are read from top to bottom. Therefore, the top two rows of numbers make up the column numbers. The third row is the variable value. The fourth and fifth rows of numbers, read vertically, identify the variable number.

For example, the value of input variable number 1 (identified by "1" in the fourth row of numbers in the first column), listed in column 01 (identified by the "0" in row one and the "1" in row two in the first column) is 5 (provided in the third row of numbers, column one). Because variable number 1 is Anxiety, as described above, the 5 indicates that the patient is experiencing significant anxiety. The next column, column 02 serves as a field separator (i.e., it provides a separator between the data fields for input variables 1 and 2). In the present embodiment, each data field in the patient file is separated by a separator as depicted in TABLE 3. Other field separators, such as commas, are well understood in the art.

The third column, column 03 contains the value of input variable number 2, which represents Depression. The value of this variable is 2, which indicates that the patient is suffering from some depression.

In one embodiment, in an actual patient data file, the patient data (i.e., the actual variable value depicted in the third row of numbers in TABLE 3) is recorded without the column number or variable number indexes. These indexes may prove helpful to human operators, but the computer 12 uses the actual variables as input. Additionally, the "Column Number", "Input Var Number" and "Out. Var Number" headings are removed.

The remainder of the input variables are represented in columns 05–77.

Columns 79–85 depicted in TABLE 3 contain the values for the output variables. For example, the value of output variable number 1, listed in column 79 is 0. This indicates that this category of care, Category 1, is inapplicable to the patient. The value of output variable number 2, listed in column 81, is 1. This indicates that the patient is identified as a utilizer of this category of care, Category 2 (i.e., the patient is seeking a combination of patient driven care and illness driven care). The remaining output variable columns (Columns 83 and 85) contain a "0" in the example depicted in TABLE 3.

As explained above, in order to train the neural network 20, expected output vectors corresponding to input vectors are provided. Accordingly, training the neural network 20 requires that a judgment be made with respect to categorizing the health care utilization of the training set of patients. Advantageously, the training set is substantially representative of the patient population. Typically, the more vectors (each vector representing one patient) provided in the training set, and the more accurate the associated expected output vectors for each input vector, the more reliable the training of the neural network.

Figure 2:
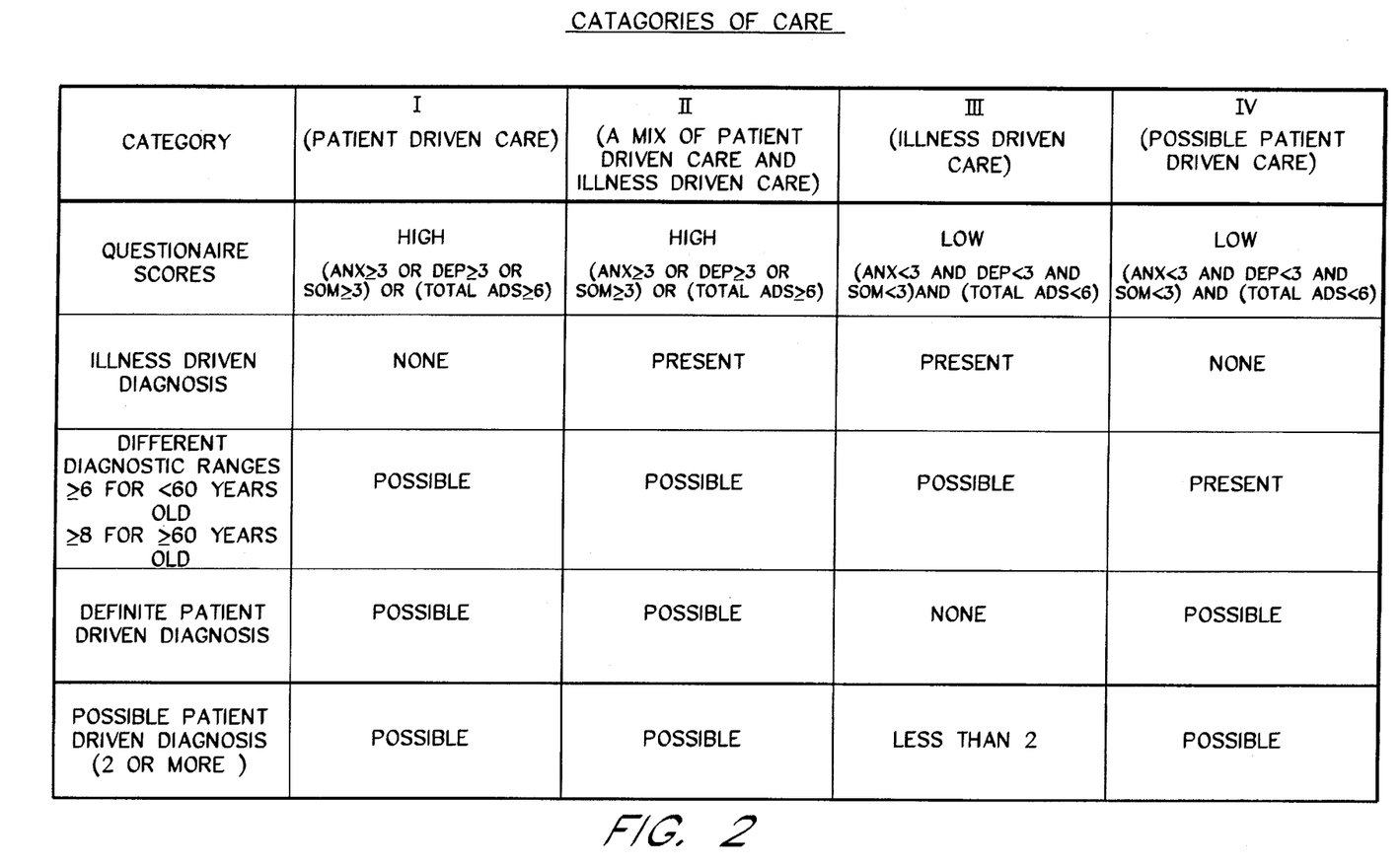
FIG. 2 is an organizational chart illustrating factors useful in categorizing health care utilization.

FIG. 2 illustrates the general factors used in the present embodiment to ascertain an expected classification of particular patients into one of four categories of care for purposes of training the neural network 20. In other words, these factors were selected to generate the original output vectors for the training set. It should be noted that the parameters used to generate the training set may or may not correlate to the function ultimately provided by the neural network 20 based upon the 21 input variables illustrated in TABLE 1. In the present embodiment, Category 1 represents Patient Driven Care, Category 2 represents a combination of Patient Driven Care and Illness Driven Care, Category 3 represents Illness Driven Care and Category 4 represents Possible Patient Driven Care.

For purposes of generating expected output vectors for the training set, a particular patient's utilization of health care is classified as Patient Driven Care, Category 1 utilization, if the patient displays all the following characteristics:

(1) the patient receives high scores on the Lifestyle Questionnaire. In the present embodiment, a patient's questionnaire scores are considered high if the patient receives:
  (a) a score equal to or greater than 3 for any of the ANX, DEP or SOM input vector variables; or
  (b) a Total ADS Score equal to or greater than 6.
(2) no illness driven diagnosis is present;
(3) The patient may have had a high number of different diagnoses categories. In the present embodiment, a patient is considered as having a high number of different diagnostic categories if the patient:
  (a) has diagnoses in six of more diagnostic ranges and is younger than 60 years old; or
  (b) has diagnoses in 8 or more diagnostic ranges, and is 60 years old or older.
(4) The patient may be diagnosed as having a definite patient driven care disorder or two or more possible patient driven care disorders.

A listing of illness driven diagnoses and definite and possible patient driven diagnoses is provided in Appendix B.

As depicted in FIG. 2, a patient's utilization is classified mixed patient driven care and illness driven care, Category 2 utilization, if the patient has the following characteristics:

(1) the patient scores highly on the questionnaire, as described above;
(2) an illness driven diagnosis is present;
(3) the patient may be diagnosed in a high number of diagnostic ranges; and
(4) The patient may be diagnosed as having a definite patient driven care disorder or two or more possible patient driven care disorders.

A patient's utilization is classified as illness driven care, Category 3 utilization, if the patient exhibits the following characteristics:

(1) the patient has low scores in the Lifestyle Questionnaire. In the present embodiment, a patient scores low on the questionnaire if
  (a) he receives a score of less than 3 on each of the ANX, DEP or SOM input vector variables; and
  (b) his Total ADS Score is less than 6.
(2) an illness driven diagnosis is present;
(3) the patient may be diagnosed in a high number of diagnostic ranges; and
(4) no definite patient driven diagnosis is present, and less than two possible patient driven care diagnoses are present.

A patient's utilization is classified as Possible Patient Driven Care, category 4 utilization, if the patient exhibits the following characteristics:

(1) patient scores low in the questionnaire, as discussed above for category 3;
(2) no illness driven diagnosis is present;
(3) the patient has been diagnosed in a high number of diagnostic ranges; and
(4) The patient may be diagnosed as having a definite patient driven care disorder or two or more possible patient driven care disorders.

Figure 3:
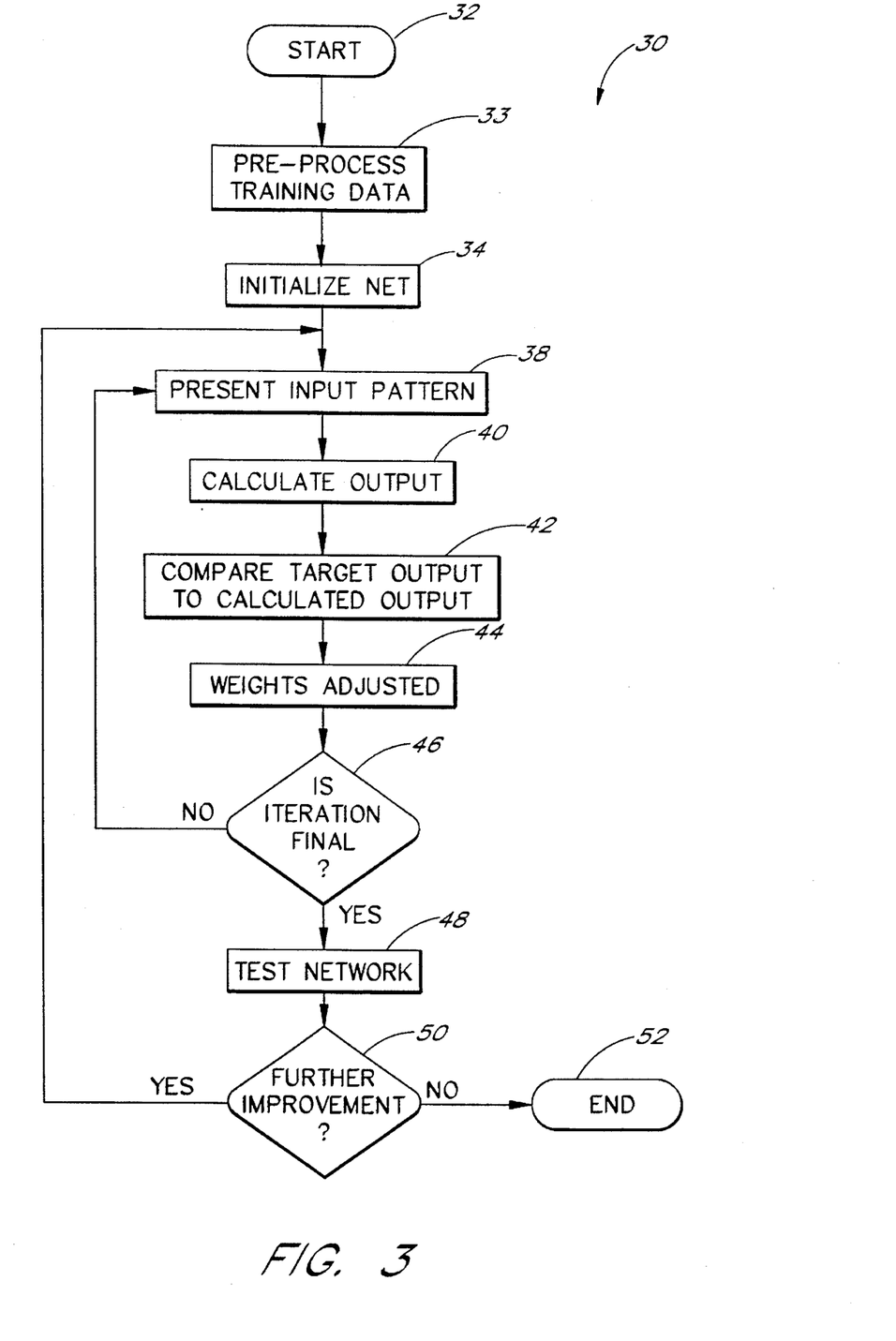
FIG. 3 depicts a flow diagram of one embodiment of the training process for a neural network processor of the present invention.

In training the neural network, many presentations of the training set and weight adjustments are required for the network to converge (become stable). During training, the neural network 20 is periodically tested to determine how well it generalizes from specific examples it has learned. To test the network, the trained net is presented with novel patient vectors, and the accuracy of the responses of the net is recorded. Training and testing proceed, until the neural network achieves the desired degree of accuracy on new input vectors or until accuracy no longer improves.

A generalized training process 30 for the neural network 20 of the present invention is depicted in the flow diagram of FIG. 3. The training process 30 begins, as represented in a start block 32. First, input and output vectors are scaled to the −1 to 1 range discussed above, and any other preprocessing of the training data is completed, as represented in an action block 33. The next step is to initialize the neural network 20, as represented in an action block 34. In this step, variables used in the neural network are initialized. In particular, the weights used for the neural network inputs and between layers are selected as random values, and the learning rate, network architecture, activation function, and other parameters are also selected.

Input vectors and their corresponding target output vectors are then presented to the neural network in random order, as represented in an action block 38. The input vectors and target output vectors are preferably read from a file created either manually by an operator via the keyboard 14 or by providing commands to the processing system 10 to retrieve the appropriate patient data files from the training set on the storage media 16. In the present embodiment, the data in the patient data files is preferably stored in a conventional ASCII format. Each data file in the training set consists of two vectors of numbers: an input vector and a target output vector. Each vector consists of a series of numbers separated by one or more blank spaces, as explained above with reference to TABLE 3. The input vector represents the patient data which is presented to the network, and the target output vector represents the target response of the network (i.e., the output which should be produced by the network in response to this input vector).

Based on the input vector, and the weights initially assigned, the neural network calculates the output response, as represented in an action block 40. Next, the neural network 20 performs a comparison between the calculated output response with the target output to provide an error signal, as represented in an action block 42; and the weights from each input are adjusted to partially compensate for the error signal, as represented in an action block 44.

The amount of compensation in the adjustment of the weights is dependent upon the selected learning rate for the neural network 20. If the learning rate is too fast, the compensation is too great for each error signal; and the neural network 20 loses what the neural network "learned" from each vector when the subsequent vector is processed. Accordingly, a learning rate between 0 and 1 is selected in the present embodiment to provide less than complete adjustment for each error signal, as well understood in the art.

Next, a determination is made whether this iteration is the last iteration before testing, as represented in a decision step 46. In other words, several iterations with the training set are generally completed before testing. If the current iteration is the last iteration, the training process 30 proceeds to testing, as represented in the action block 48. If the iterative process is not complete, the neural network 20 repeats the steps represented in the action blocks 38–46, until all vectors in the training set have been presented to the neural network 20 a number of times.

When the iterative process depicted by steps 38–46 has completed (decision block 46), the neural network 20 is tested, as represented in the test network action block 48. In this step, the neural network 20 receives new input vectors, not part of the training set. The output response of the neural network 20 is then calculated and compared to a target response. If the neural network 20 produces accurate results, the operator may determine that training is adequate, as represented in a decision block 50, and the training process is complete, as represented in an end block 52. If the result is unacceptable and further improvement is desired, the neural network 20 repeats steps 38–46 for a new training set, or for the original training set, or a combination of some or all of the original training set with additional new input vectors.

A variety of network models may be used in the neural network 20. Typical models include the back-propagation network, the radial basis function network and the learning vector quantization network, as known in the art. For each neural network type, the appropriate training processes is utilized, as well understood in the art.

After the neural network 20 is trained, it may be used to process new information (new input vectors). In one embodiment of the present invention, prior to utilizing the trained neural network 20 to analyze health care utilization of patients, patient information may be preprocessed to identify patients who are at "high risk." In the present embodiment, high risk patients are those patients considered to be suffering from an immediate threat to their health.

Figure 4A:
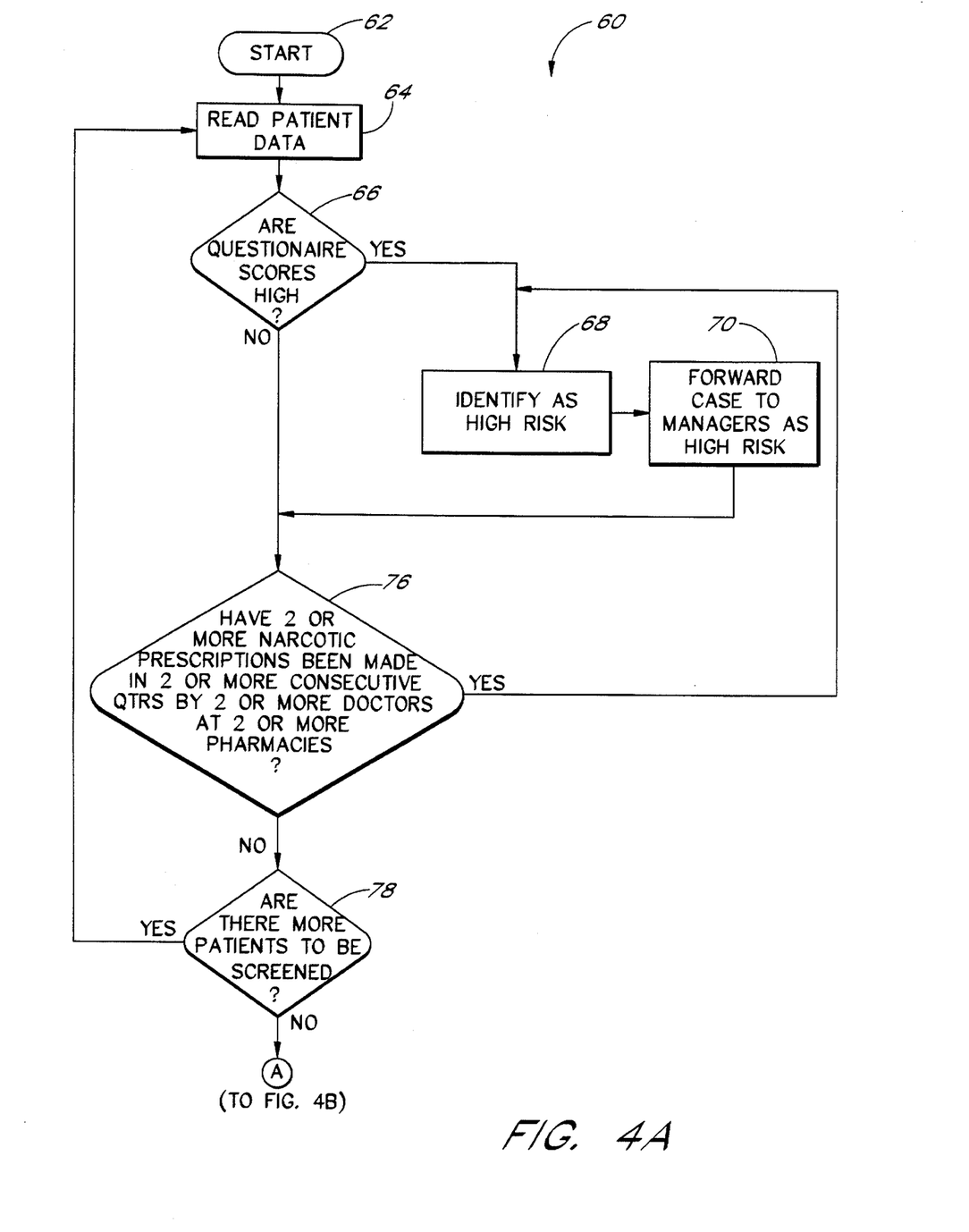
FIGS. 4A and 4B depict a flow diagram of one embodiment of a patient prescreening process of the present invention.
Figure 4B:
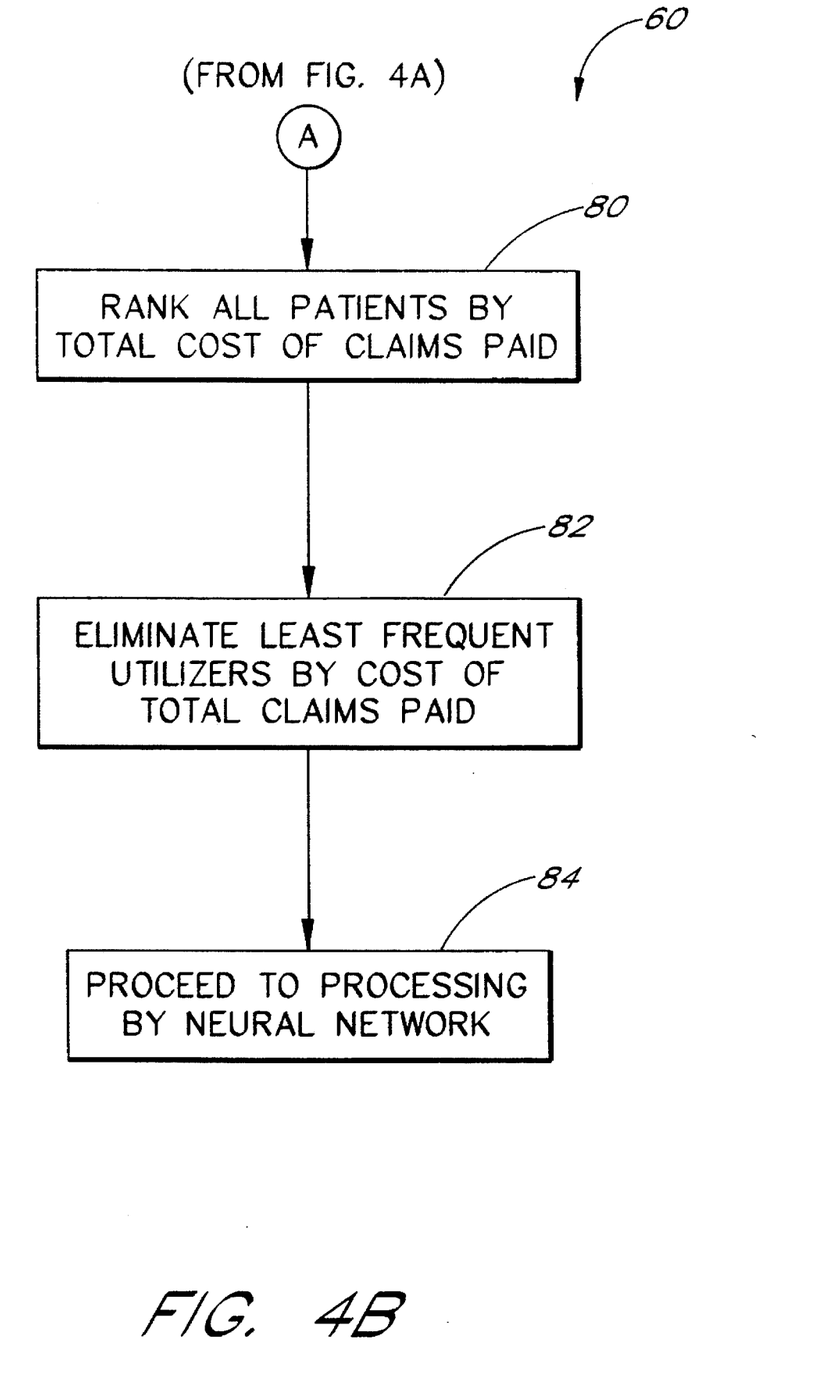

The flow diagram of FIGS. 4A and 4B illustrate one possible embodiment of a prescreening process 60 in accordance with the present invention. Beginning at a start block 62, the process proceeds to a read patient data action block 64. Patient data is accepted via keyboard input and/or via data files. As represented in a decision block 66, a determination is made whether the patient has "high" Lifestyle Questionnaire scores, a represented in a decision block 66. In the present embodiment, a patient is considered to have a high Lifestyle Questionnaire score if a "CAGE" score is greater than or equal to 2, a MEBS score is greater than or equal to 8, or a score is equal to or greater than 3 on any one of the ANX, DEP or SOM input variables or a total ADS score is equal to or greater than 6.

The CAGE score is obtained from the Lifestyle Questionnaire, and relates generally to psychological problems due to alcohol addiction. With reference to the Lifestyle Questionnaire in Appendix A, four questions in the Questionnaire relate to the CAGE score. Specifically, Questions 16 through 19 inquire whether (1) the patient has ever felt that he should Cut Back on his drinking, (2) if the patient has ever been Annoyed by others' criticisms of his drinking, (3) if the patient has ever felt Guilty about his drinking habits and (4) if the patient has ever consumed alcohol as soon as he wakes up so as to steady his nerves or to overcome a hangover. A score of "1" is assigned to each affirmative response and a score of "0" is assigned to each negative response. CAGE stands for "Cut back, Annoyed, Guilty, Eye Opener," which are attributes related to alcoholism. The total from the four questions provides the patient's total CAGE score. If the CAGE score is equal to or greater than 2, the patient is identified as having a high Lifestyle Questionnaire score.

The MEBS score is also obtained from the Lifestyle Questionnaire. As seen in the Lifestyle Questionnaire, ten questions (questions 5 through 14) relate to MEBS. These questions relate to a patients caffeine usage. If the patient answers yes to eight or more of questions 5 through 14, the patient is identified as having a high Lifestyle Questionnaire score.

The patient scores for ANX, DEP and SOM are also obtained from the Lifestyle Questionnaire. As seen in the Lifestyle Questionnaire, questions 21–25 relate to anxiety (ANX), questions 26–30 relate to depression (DEP) and questions 31–35 related to somatization (SOM). As explained above, if a patient has three or more yes answers in any of the ANX, DEP or SOM categories of questions, or has a combined total of six or more for all three categories, the patient is identified as having a high Lifestyle Questionnaire score.

Any patient identified as having a high Lifestyle Questionnaire score is identified as being at high risk, as represented in an action block 68. This information is then forwarded to a case manager, as represented in an action block 70. The case manager may automatically receive this information via a computer network, or the operator for the pre-processing system may provide this information to the case manager.

It should be understood that data for all patients could be pre-processed before the case manager is notified. For instance, each patient that is to be forwarded to a case manager could be identified in the pre-processing; and a list of all such patients, with corresponding recommendations, forwarded to the case manager.

However, if a patient's Lifestyle Questionnaire score is not high (decision block 66), or the high risk identification is complete (action block 68), those patients who appear to have a narcotic dependency problem are identified, as represented in a decision block 76. If a patient has been provided with two or more narcotic prescriptions in two or more consecutive quarters by two or more doctors at two or more pharmacies, the patient is identified as being at high risk, as represented in the action block 68. This information is then forwarded to the case manager, as illustrated in the action block 70.

It should be understood that the Lifestyle Questionnaire data and pharmacy (narcotic) data from all patients could be pre-processed before the case manager is notified.

If the patient's records do not suggest a narcotic dependence (decision block 74), a determination is made whether more patients are available for pre-screening, as represented in a decision block 78. If more patients are available for screening, the steps represented in block 64–78 are repeated.

If no further patient files are available, patients are ranked according to the total cost of claims paid for the patient group under consideration, as represented in an action block 80 (FIG. 4B, via continuation point A). Next, patients with the least frequent utilization are eliminated as unlikely candidates for inappropriate utilization. In the present embodiment, the top 10% (dollar amount) for total claims paid for the group under consideration are kept for consideration. The bottom 90% (by total dollars of claims paid) are removed from consideration.

In one embodiment, only the top 10% of utilizers are processed by the neural network 20, as represented in an action block 84. Alternatively, all patients are passed to the neural network 20 for processing. Pre-screening for high risk may be advantageous even when all patients are analyzed with the neural network 20, in that the case manager receives a quick indication of the likelihood of problems.

Figure 5:
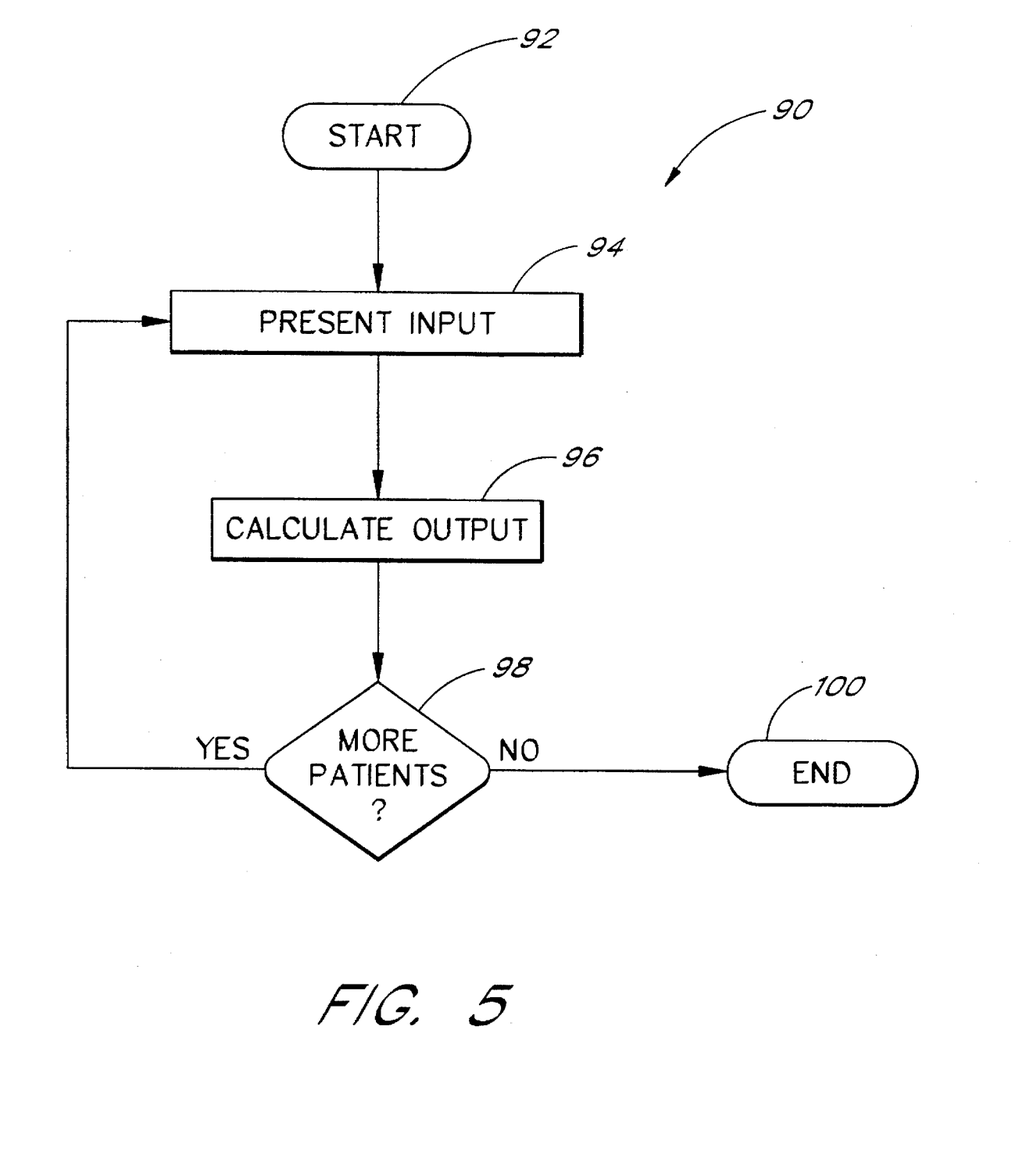
FIG. 5 depicts a generalized flow diagram of one embodiment of the overall operational process of the present invention.

The flow diagram of FIG. 5 illustrates a generalized operational process 90 for the trained neural network 20. Beginning at a start block 92, control proceeds to an action block 94. As represented in the action block 94, the patient input vector is presented to the trained neural network 20. The neural network 20 calculates the output vector for the selected patient, as represented in an action block 96. Next, a determination is made whether all patients, from a group of patients to be analyzed, have been analyzed by the neural network 20, as represented in a decision block 98. The neural network repeats the processing until all patients have been analyzed. The process completes in an end block 100.

The output vector for each patient is advantageously stored in the patient's data file, or in a separate file categorizing patients by their category of health care utilization. Those patients who have been classified in Category 1, Category 2 or Category 4 are forwarded to case managers for further examination in an attempt to identify inappropriate usage, and to treat the underlying problems for the patients.

It will be understood, that for each patient continually utilizing health care in an inappropriate way, many health care dollars will be spent in treatments which will not assist in the underlying problem. Thus, by characterizing patients as having the potential of inappropriate utilization, the case managers can assist in obtaining proper diagnoses, and eliminating the unnecessary expenses of treating ailments which merely stem from the underlying problem.

Although the present invention has been described in terms of certain preferred embodiments, other embodiments can be readily devised by one skilled in the art in view of the foregoing. For instance, processing methods other than neural networks may be appropriate given the factors suggesting utilization characteristics depicted in FIG. 2. Additionally, further factors may also be considered in making the above determinations. Accordingly, the scope of the present invention is defined by reference to the appended claims.

APPENDIX C

OUTPATIENT
ICD 9 CODES & CLASSIFICATION

| | |
|---|---|
| 001–139 | Infectious and Parasitic Disease |
| 140—230 | Neoplasms |
| 240–279.9 | Endocrine, nutritional and metabolic diseases |
| 280–289 | Immunity diseases; diseases of the blood and blood forming organs |
| 290–319 | Mental disorders |
| 320–389 | Diseases of the nervous system and sense organ |
| 390–459 | Diseases of the circulatory system |
| 460–519 | Diseases of the respiratory system |
| 520–579 | Diseases of the digestive system |
| 580–629 | Diseases of the genitourinary system |
| 630–676 | Complications of pregnancy, childbirth and the puerperium |
| 680–709 | Skin and subcutaneous tissue |
| 710–739 | Diseases of the musculoskeletal system & connective tissue |
| 740–759 | Congenital anomalies |
| 760–779 | Certain conditions originating in the perinatal period |
| 780–799 | Symptoms, signs and ill defined conditions |
| 800–999 | Injury and poisoning |
| | E Codes |
| | V Codes |

APPENDIX A

Rev 5/92                    OCHSNER LIFESTYLE QUESTIONNAIRE
    Patient Name          Age/Sex
    Clinic Location       Date
    Clinic #                   OHP #

|  | Yes | No | Office Use |
|---|---|---|---|
| Please answer Yes or No to each question. | | | |

1. Do you smoke cigarettes? If yes, how many per day?
2. Do you usually use your seatbelt while driving or riding in a car?
3. Do you exercise vigorously three or more times per week?
4. Do you regularly drink caffeinated coffee, a "cola" or tea? If No, skip to Question 15. If yes continue.
5. Does drinking coffee, a "cola," or tea make you feel good in some way or relax APPENDIX A-continued Rev 5/92                   OCHSNER LIFESTYLE QUESTIONNAIRE Patient Name          Age/Sex
Clinic Location       Date
Clinic #                 OHP # you?
6. Are you able to drink coffee, "cola," or tea and go right to sleep?
7. Do you feel you must have coffee/cola/tea in the morning?
8. If you don't have your usual morning coffee/cola/tea, do you feel any of the following?
   a) Irritable or grouchy
   b) Fatigued, listless, no energy
   c) Decreased attention and concentration
9. If you don't drink your usual morning coffee/cola/tea, do you experience any of the following?
   a) Headache
   b) Runny nose or head congestion
   c) Decreased attention and concentration
10. Do you typically drink any coffee/cola/tea in the afternoon?
11. Do you typically drink any coffee/cola/tea in the evening?
12. Do you drink more than 5 cups of coffee (4 mugs), or more than 10 colcas or teas per day?
    How many cups of coffee do you drink per day?
    How many colas or teas do you drink per day?
13. Do you take any medicines regularly that contain caffeine, such as Excedrin, Dristan, Vivarin, appetite suppressants?
14. Have you ever made an unsuccessful attempt at reducing or stopping your caffeine intake?                                               MEBS4
15. Do you drink alcoholic beverages?
    If Yes, how many drinks per week?
16. Have you ever felt you ought to cut down on your drinking?
17. Have people annoyed you by criticizing your drinking?
18. Have you ever felt bad or guilty about your drinking?
19. Have you ever had a drink first thing in the morning to steady your nerves or get rid of a hangover?                                              CAGE2

DWI 20. Have you received 2 or more DWI's in your lifetime?
21. Have you been especially nervous or anxious during the past three months?
22. Have you been worrying a lot about bad things that might happen?
23. Have you ever had a panic attack, an episode when you suddenly felt anxious, frightened, or extremely uncomfortable?
24. Are you bothered by thoughts, images, or impulses that keep coming back to you even when you try not to have them?
25. When you are feeling especially anxious or nervous, do you also feel keyed up or irritable or have difficulty concentrating or sleeping?                  ANX
26. Do you currently feel depressed or down nearly every day?
27. Do you feel tired alot or lacking in energy?
28. Do you feel hopeless at times?
29. Are you down on yourself, feeling worthless or a failure?
30. Have you noticed a change in your appetite (either poor appetite or overeating)?                                                                    DEP
31. Have you seen a doctor or taken prescription medication for any of the following symptoms:
    a) Vomiting (other than during pregnancy)
    b) Pain in extremities
    c) Shortness of breath when not exerting oneself
    d) Amnesia
    e) Difficulty swallowing
    f) Burning sensation in sexual organs or rectum (other than during intercourse)
32. Do you worry a lot about your physical health?
33. Have physical problems limited your social or occupational activities in any way?
34. Have you often gone to the doctor with physical problems, only to find that the doctor could not explain or diagnose the problem?
35. Before age 30, did you have a lot of physical probelms or illnesses or believe you were sickly?                                                                  SOM
36. please list any currnt illnesses or diseases, such as high blood pressure, diabetes, heart disease, cancer, etc.:

_________________________________________

_________________________________________

Thank you for your time and cooperation in completing this questionairre.

What is claimed is:

1. A system to aid in identifying patients potentially seeking inappropriate health care, said system comprising:

a plurality of patient characteristics for a plurality of patients, said patient characteristics representing medical usage and psychological information about said patients; and a neural network responsive to input variables generated from said plurality of patient characteristics, said neural network configured to categorize the plurality of patients according to utilization characteristics of said patients based on said input variables, one category of utilization characteristics identifying patients who are potentially seeking inappropriate health care.

2. A method for categorizing health care utilization of a plurality of patients, said method comprising the steps of:

defining a set of input variables having input values which define selected characteristics of each of the plurality of patients;

forming an input vector for a neural network based upon said set of input variables for each of the plurality of patients; and analyzing said input vector with said neural network to categorize the health care utilization of at least some of the plurality of patients into at least one of a selected plurality of health care utilization categories.

3. The method of claim 2, wherein said at least one of said selected plurality of health care utilization categories identifies patients who are seeking inappropriate health care.

4. The method of claim 2, wherein at least one of said input variables corresponds to certain aspects of the psychological condition of one of said patients.

5. The method of claim 2, wherein at least one of said input variables corresponds to the diagnoses categories of one of said patients.

6. The method of claim 2, wherein said categories are selected from the group consisting of: patient driven care, illness driven care, a mix of patient driven care and illness driven care, and possible patient driven care.

7. The method of claim 6, wherein said input variables form an input vector to a neural network trained to categorize patients according to health care utilization based upon said input variables.

8. The method of claim 7, wherein at least one of set of pre-screening variables comprises a first variable indicative of the existence of at least one alcohol or drug addiction disorder.

9. A method for training a neural network to categorize health care utilization of a plurality of patients, said method comprising the steps of:

(a) defining a set of input variables having input values which define selected characteristics of each of a plurality of patients, said plurality of patients forming a training set;

(b) defining at least two categories of health care utilization for said patients;

(c) selecting which of said at least two categories applies to each of said plurality of patients;

(d) providing said input variables for each patient and the selected category for each patient, to the neural network, the selected category for each patient category forming a target output value;

(e) analyzing the input variables with the neural network to obtain a first output value associated with said set of input variables;

(f) comparing said first output value with said target output value;

(g) adjusting weights in the neural network if said first output value does not equal said target output value to partially compensate for the difference between the target output value and the first output value; and (h) repeating steps (d) through (g) for each of said plurality of patients in the training set until said first output value is substantially the same as said target output value or no more improvement is attained.

* * * * *